(12) United States Patent
Iketaki

(10) Patent No.: US 7,812,967 B2
(45) Date of Patent: Oct. 12, 2010

(54) MICROSCOPY METHOD AND MICROSCOPE

(75) Inventor: Yoshinori Iketaki, Oume (JP)

(73) Assignee: Olympus Corporation, Tokyo (JP)

( * ) Notice: Subject to any disclaimer, the term of this patent is extended or adjusted under 35 U.S.C. 154(b) by 400 days.

(21) Appl. No.: 11/847,943

(22) Filed: Aug. 30, 2007

(65) Prior Publication Data
US 2008/0151239 A1    Jun. 26, 2008

(30) Foreign Application Priority Data
Dec. 26, 2006    (JP)    ............ 2006-349694

(51) Int. Cl.
*G01N 21/41* (2006.01)

(52) U.S. Cl. .................................... 356/517

(58) Field of Classification Search .......... 356/450–521
See application file for complete search history.

(56) References Cited

U.S. PATENT DOCUMENTS

| | | | |
|---|---|---|---|
| 3,999,854 A * | 12/1976 | Barrett | .......... 356/454 |
| 5,731,588 A | 3/1998 | Hell et al. | |
| 5,777,342 A | 7/1998 | Baer | |
| 5,866,911 A | 2/1999 | Baer | |
| 6,122,058 A * | 9/2000 | Van Der Werf et al. | ..... 356/635 |
| 6,157,320 A | 12/2000 | Yujiri et al. | |
| 6,194,486 B1 | 2/2001 | Yujiri et al. | |
| 6,667,830 B1 | 12/2003 | Iketaki et al. | |
| 6,859,313 B2 | 2/2005 | Iketaki et al. | |
| 7,388,668 B2 * | 6/2008 | Potma et al. | ........... 356/451 |

FOREIGN PATENT DOCUMENTS

| | | |
|---|---|---|
| DE | 199 80 759 T1 | 10/2001 |
| JP | 10-331122 A | 12/1998 |
| JP | 3020453 A | 1/2000 |

\* cited by examiner

*Primary Examiner*—Tarifur Chowdhury
*Assistant Examiner*—Jonathon D Cook
(74) *Attorney, Agent, or Firm*—Holtz, Holtz, Goodman & Chick, PC

(57) ABSTRACT

The present invention provides a microscopy method and a microscope, which enable microscopic observation of desired information of a specimen with an extremely high S/N ratio in a short period of time without increasing intensity of a light sources. The method of the invention is characterized in that it comprises: a simultaneous irradiation step of irradiating a specimen with first and second electromagnetic rays having different wave length with the rays overlapping at least partly each other; and a simultaneous irradiation visualization step of visualizing a spatial distribution of a refractive index variation caused by the irradiation of the first electromagnetic ray as a phase contrast image of the second electromagnetic ray having passed through the specimen in the region of the specimen to which the overlapped the first and the second electromagnetic rays are irradiated.

23 Claims, 9 Drawing Sheets

(a)

(b)

(a)

(b)

IR-visible Double Resonance Dispersion

Normal Dispersion (a)

(b)

MICROSCOPY METHOD AND MICROSCOPE

BACKGROUND OF THE INVENTION

1. Field of the Invention

The present invention relates to a microscopy method and a microscope, which use electromagnetic rays of two wavelengths. This application is based on Japanese Patent Application No. 2006-349694, the content of which is incorporated herein by reference.

2. Description of the Related Art

The technology of the optical microscope has a long history, and various types of microscopes have been developed. Moreover, in recent years, a further highly functional microscope system is being developed due to advancement of peripheral technologies including laser and electronic imaging technologies. Particularly, in the field of nanobioscience, there has been developed a microscopic measurement method which uses illuminating lights of two different wavelengths. In this microscopic measurement method, two laser beams of different wavelengths are overlapped and converged onto a specimen simultaneously, and photoresponsive data such as scattering light and fluorescence from the specimen is measured. The method attracts attention as a measurement method to analyze optical responses in the time domain as well as spatial measurement simultaneously.

A known typical microscopic measurement method uses plural light sources to irradiate pulsed laser beams of different wavelength onto a specimen, and then detects photoresponsive signals including fluorescence emitted from the irradiated domain. One example of such a method is an IR-visible double resonance microscopy using double resonance of infrared light and visible light (For example, refer to Japanese Patent Number 3020453).

In this IR-visible double resonance microscopy, fluorescent molecules in the ground state S0 is excited to high-vibrational excited state S0' belonging to the ground state by irradiation of infrared light as shown in FIGS. 9 (a) and (b). The activated molecules are further activated to upper electron-excited state S1 by irradiating visible light. The molecules thus activated to S1 state generate fluorescence, and relax back to the ground state S0.

In this IR-visible double resonance microscopy, for example, pulsed infrared light and pulsed visible light are focused at the same region of a specimen, and the focus points are two-dimensionally scanned on the specimen relatively and fluorescence signals at each focus point are measured to form two-dimensional fluorescence image in a computer. In this case, fluorescence cannot be produced unless S0' state of the molecules is generated by the resonance with the infrared light, therefore the obtained fluorescence image shows spatial distribution of the molecules in infrared vibrationally excited state.

The characteristic of this microscopy method is that it can observe spatial distribution of the molecules in the infrared vibrationally excited state with the resolution of visible light (i.e. a few to several hundreds of nano meters), while the spatial resolution in conventional infrared microscopic spectroscopy is limited by infrared diffraction limit, i.e. a few to several microns.

An example to detect distribution of CH groups in rhodamine 6G molecules included in a specimen will be discussed below, as a specific example. A rhodamine 6G molecule has side-chain CH groups as shown in the molecular structure in FIG. 10(a), and it has an absorption band, for example, in the vicinity of 3200 $cm^{-1}$ (wave length: 3.1 μm, photon energy: 0.4 eV) due to CH breathing vibration. In addition, the wavelength corresponding to the transition/absorption from the ground state S0 to electron-excited state S1 is 532 nm (photon energy: 2.33 eV).

Thus, rhodamine 6G molecules are excited to the vibration-rotation level S0', where v=1, belonging to the ground state by means of infrared ray with wavelength of 3.1 μm as shown in the diagram in FIG. 10 (b). Then, they are doubly-excited by a laser beam (visible light) with the wavelength (approx. 640 nm) corresponding to the energy gap from the S0' state to the S1 state, i.e. 1.9 eV.

As a result, rhodamine 6G molecules finally reach the electron-excited state S1, and then they will emit fluorescence and relax to the ground state S0. This fluorescence process does not occur unless the visible light and the infrared light overlap each other on the specimen in terms of space and time. In addition, both wavelengths of the visible light and the infrared light need to correspond to the energy gaps or wavelength between molecular quantum states. In other words, the visible light and the infrared light must satisfy the condition of double resonance absorption of the rhodamine 6G molecules.

Thus, the fluorescence is not detected when the infrared light does not exist. Since infrared absorption by the CH breathing vibration occurs and the fluorescence is emitted only when both the infrared light and the visible light exist, the fluorescence image to be obtained is equivalent to the visualized spatial distribution of vibrational excited state of the CH groups.

In general, molecules have various chemical groups besides CH group such as OH, SH, NH and the like, and each of these chemical groups has its characteristic resonant frequency. Therefore, if wavelengths of the visible light and the infrared light are synchronized for each chemical group, it will be possible to obtain a fluorescence image corresponding to spatial distribution of the each chemical group.

The spatial region from which the fluorescence signals are emitted is an overlap region of the visible and infrared lights despite the optical response of the specimen being in the infrared domain, therefore the spatial resolution of the fluorescence image to be obtained is determined by the diffraction limit of the visible light. For example, if the wavelength of a visible light is 500 nm and a numerical aperture of an object lens of a microscope is 1.4, spatial resolution of nearly 200 nm can be achieved.

Even more particularly, in terms of spatial resolution, it is also possible to configure the microscope to have depth resolution. More specifically, because the fluorescence signals are obtained only from the vicinity of the focal plane where visible light and infrared light are converged simultaneously with sufficient intensity, three-dimensional cross-sectional image can also be obtained by moving the specimen along optical axis with respect to the focus position.

In addition, if the light sources of the visible light and the infrared light are pulsed light sources, fluorescence signals are obtained only when these light sources are overlapped also in a time domain. Therefore, by shifting the timing of pulsed oscillations between the visible light and the infrared light, it will also be possible to trace a time response in regard to a relaxation process of a vibrational-excited state.

However, according to the experimental examination conducted by the present inventor, it becomes clear that there are some points to be improved in detection methods of the conventional light response signal, as described below. At first, because the detection methods described above basically detect the fluorescence, the molecules as observation objects are required to have high fluorescence efficiency. Consequently, in a living specimen, observation objects are limited to autofluorescent molecules. Moreover, in order to observe non-autofluorescent molecules, the observation object need to be, for example, stained by a fluorescent dye.

In addition, because molecules excited to S1 state can emit fluorescence of one photon per one molecule theoretically, the quantity of detection signals is determined by the number of excitation and fluorescence yield during the light irradiation. Moreover, during the excitation cycle, discoloration of molecules occurs and therefore the quantity of signals is suppressed. As a result, the S/N ratio may deteriorate remarkably, and in order to improve the S/N ratio, longer measurement time and/or higher light source intensity will be required.

SUMMARY OF THE INVENTION

Thus, the object of the present invention, which has been done in view of these points, is to provide a microscopy method and a microscope which enable microscopic observation of desired information in a specimen with an extremely high S/N ratio in a short period of time without increasing intensity of light sources.

The first aspect of the invention, which achieve the object described above, is a microscopy method comprising: a simultaneous irradiation step of simultaneously irradiating a specimen with first and second electromagnetic rays having different wavelength with the rays overlapping at least partly each other; and a simultaneous irradiation visualization step of visualizing a spatial distribution of a refractive index variation caused by the irradiation of the first electromagnetic ray as a phase contrast image of the second electromagnetic ray having passed through the specimen in the region of the specimen to which the overlapped first and second electromagnetic rays are irradiated.

The second aspect of the invention resides in the microscopy method as set forth in the first aspect, wherein the first electromagnetic ray has a wavelength or photon energy that excites a predetermined substance in the specimen from the ground state to a vibrational-rotational level belonging to the ground state.

The third aspect of the invention resides in the microscopy method as set forth in the second aspect, wherein the second electromagnetic ray has photon energy at least less than the difference between energy to excite the predetermined material in the specimen from the ground state to the first electron-excited state and energy to excite the material from the ground state to the vibrational-rotational level belonging to the ground state.

The fourth aspect of the invention resides in the microscopy method as set forth in the first, second or third aspect, wherein the domain irradiated by the second electromagnetic ray in the specimen is smaller than the domain irradiated by the first electromagnetic ray.

The fifth aspect of the invention resides in the microscopy method as set forth in any one of the first to fourth aspects, wherein the specimen is stained by molecules which have vibrational-rotational level vibrationally excitable with the first electromagnetic ray.

The sixth aspect of the invention resides in the microscopy method as set forth in any one of the first to fourth aspects, wherein the specimen is stained by molecules of which the energy difference between the first electron-excited state and the vibrational-rotational level belonging to the ground state is greater than the photon energy of the second electromagnetic ray.

The seventh aspect of the invention resides in the microscopy method as set forth in any of the first to fourth aspects, wherein the specimen has a vibrational-rotational level vibrationally-excitable with the first electromagnetic ray, and wherein the specimen is stained by molecules of which the energy difference between the first electron-excited state and the vibrational-rotational level belonging to the ground state is greater than the photon energy of the second electronic magnetic ray.

The eighth aspect of the invention resides in the microscopy method as set forth in the second aspect, wherein the predefined substance in the specimen is a non-fluorescent molecule.

The ninth aspect of the invention resides in the microscopy method as set forth in any of the second to eighth aspects, wherein the specimen comprises molecules including any of the chemical groups: $C=C$, $C=C$, $C=C=C$, $C=C=C=C$, $CH$, $CO$, $C-C$, $C\equiv N$, $C-C\equiv C$, $N=C=O$, $N=C=N$, $C=N$, $NNN$, $N=N$, $C-N$, $ONO$, $N=O$, $O-O$, $SH$, $CS$, $S-S$, $SO_2$, $S=O$, $C-S-C$, $OH$, $NH$, $CO_3$, $CH_3-C$, $CH-(C=O)$, $-CH_2-$, $-CH_2-(C=O)$, $-CH_2-(C=N)$, $>C=CH_2$, $>C=CH-$, $-C=C-H$, $-C\equiv C-$, $-CO-OH$, $P=O$, $Si-CH_3$, $CF$, $CCl_2$, $CCl_3$, $P=S$, $Si-C$, $CH_2-S-CH_2$, $C_6H_6-O-P$, $R-O-SO_2-O-R$, $R-O-SO_2-R$, $H-CO-O-R$, $-CH_3-CO-C-R$, $=CH-CO-O-R$, $C_6H_6-CO-O-R$, $CH_2-CHO$, $C_6H_6-CHO$, $CH_2-CO-CH_2$, $C_6H_6-CO-C$, $C-CO-CO-C$, $-CO-NH_2$, $-CO-NH-R$, $-CO-NR_2$, $CH_2-NH_2$, $>CH-NH_2$, $C_6H_6-NH_2$, $CH_2-NH-CH_2$, $CH-NH-CH$, $(CH_2)_3N$, $C_6H_6-N-R_2$, $>C=NH$, $>C=N-C$, $-C\equiv N$, $PH$, $SiH$, $O=C(O-R)_2$, $HN=C(O-R)_2$, $R-O-NO_3$, $R-NO_2$, $R-O-NO$, $CH_2-O-CH_2$, $C_6H_6-O-CH_3$, $CH_2-OH$, $CH-OH$, $C-CH$, $C_6H_6-OH$, $R-SO-R$, $R-SO_2-R$, $R-SO_2-NH_2$.

The tenth aspect of the invention resides in the microscopy method as set forth in the eighth or ninth aspect, wherein the molecules include lone electron excitation.

The eleventh aspect of the invention resides in the microscopy method as set forth in the first aspect, wherein the wavelength of the first electromagnetic ray exists within the range of the resonant absorption band corresponding to the excitation transition of the predetermined substance in the specimen from the ground state to the first electron-excited state.

The twelfth aspect of the invention resides in the microscopy method as set forth in the eleventh aspect, wherein the second electromagnetic ray has photon energy less than excitation energy required for the transition of the predetermined substance in the specimen from the first electron-excited state to another excited state of higher energy level than the first electron-excited state.

The thirteenth aspect of the invention resides in the microscopy method as set forth in the twelfth aspect, wherein the second electromagnetic ray belongs to the range of wavelength that is out of fluorescence wavelength range.

The fourteenth aspect of the invention resides in the microscopy method as set forth in the thirteenth aspect, wherein the wavelength of the first electromagnetic ray exists within the range of the resonant absorption band corresponding to the excitation transition of the predetermined substance in the specimen from the ground state to the first electron-excited state, and wherein the specimen is stained by molecules of which the energy required for the transition from the first electron-excited state to another electron-excited state of higher energy level than the first electron-excited state is greater than the photon energy of the second electromagnetic ray.

The fifteenth aspect of the invention resides in the microscopy method as set forth in any of the first to fourteenth aspect, further comprising: a separate irradiation step of irradiating the specimen with the second electromagnetic ray solely; a separate irradiation visualization step of visualizing a spatial distribution of a refractive index variation generated in the region of the specimen irradiated by the second electromagnetic ray in the separate irradiation step as a phase contrast image; and difference image generation step of generating the difference image between the phase contrast image in the simultaneous irradiation visualization step and the phase contrast image in the separate irradiation visualization step.

Furthermore, the sixteenth aspect of the invention, which achieve the object described above, is a microscope characterized in that it comprise: a first radiation source generating first electromagnetic ray; a second radiation source generating second electromagnetic ray with different wavelength from that of the first electromagnetic lay; an illumination optical system configured so that the first electromagnetic ray generated from the first radiation source and the second electromagnetic ray generated from the second radiation source are irradiated to the specimen with the rays overlapping at least partly each other; and a detection means for visualizing a spatial distribution of a refractive index variation caused by the irradiation of the first electromagnetic ray as a phase contrast image of the second electromagnetic ray passing through the specimen in the region of the specimen to which the overlapped first and second electromagnetic rays are irradiated.

The seventeenth aspect of the invention resides in the microscope as set forth in the sixteenth aspect, wherein the first radiation source and/or the second radiation source comprise a wavelength-tunable laser light source.

The eighteenth aspect of the invention resides in the microscope as set forth in the sixteenth or seventeenth aspect, wherein the first radiation source and/or the second radiation source are pulsed light sources.

The nineteenth aspect of the invention resides in the microscope as set forth in the sixteenth or seventeenth aspect, wherein the first radiation source and the second radiation source comprise pulsed light sources which can relatively adjust radiation periods of the first electromagnetic ray and the second electronic magnetic ray respectively.

The twentieth aspect of the invention resides in the microscope as set forth in any of the sixteenth to nineteenth aspects, wherein the detection means includes a means for eliminating the first electromagnetic ray having passed through the specimen.

DESCRIPTION OF THE PREFERRED EMBODIMENTS (Abstract of the invention) At first, the invention will be outlined below by taking IR-visible double resonance microscopy as an example before explaining embodiments of the invention.

In an example of the present invention, a phase contrast detection method is introduced into the IR-visible double resonance microscopy. The phase contrast detection method is superior in its detection sensitivity. Paying attention to this point, an image is created from the change in the phase difference accompanied by an optical response process in IR-visible double resonance in exemplified embodiments of the present invention.

Figure 1:
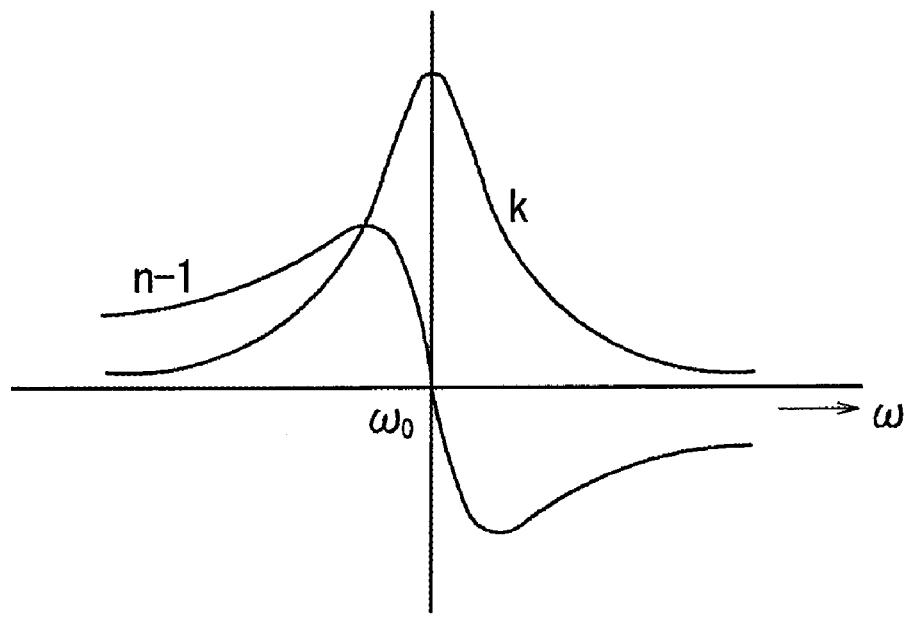
FIG. 1 shows refractive index distribution in the vicinity of an absorption edge in a molecule.

FIG. 1 shows refractive index distribution in the vicinity of an absorption edge in a molecule. In FIG. 1, an abscissa axis represents frequency of light ($\omega$), where larger $\omega$ means shorter wavelength. $\omega_0$ denotes the frequency corresponding to the maximum absorption in a resonance absorption band. In addition, while n denotes the real part of a refractive index, k denotes the imaginary part (so-called absorption coefficient). Here, n−1 denotes quantity of a variation with respect to a refractive index in vacuum, and the larger the quantity of a variation become, the larger the phase delay in the medium become.

In an ordinary phase contrast microscopy, n−1 in a transparent region with small k is converted to light amplitude to create an image.

Figure 2:
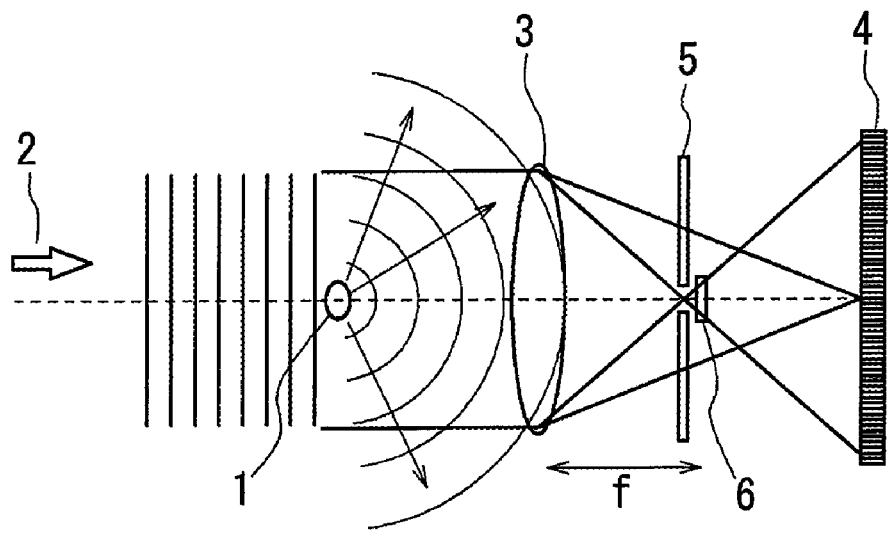
FIG. 2 is a figure to explain a principle of a phase contrast microscopy method.

FIG. 2 shows a figure to explain a principle of a phase contrast microscopy method. In FIG. 2, an irradiating light 2 of a plane wave is incident upon an observation specimen 1, which is a phase object, and then scattered by the observation specimen 1 to generate a spherical surface wave having amplitude in proportion to n−1 with the observation specimen 1 being as its origination.

The generated spherical wave forms an image on two-dimensional detector 4 by an object lens 3. At the same time, the rest of the plane wave which is not scattered firstly converge at the focus position on the image side at the distance f apart from the object lens 3, and then spread to reach detector 4. A quarter-wave ($\lambda/4$) plate 5 with a minute pinhole is placed at the focus position on the image side of the object lens 3, and an attenuation filter 6 of the size approximately same as the minute pinhole is placed adjacent to the pinhole.

In a phase contrast microscopy method, basically, the scattered spherical wave and the non-scattered light (irradiating light) interfere with each other, and the phase difference is converted to light and shade of amplitude intensity. According to the scattering theory (for example, Shigenobu Sunakawa, "theoretical electromagnetism" Kinokuniya, 1973, p 235), the scattered light has phase lag of a quarter-wavelength ($\lambda/4$) and have an amplitude in proportion to a phase lag ($\delta$) caused by difference of refractive index by the scattering.

In order to compensate this quarter-wavelength phase lag between the spherical wave and the non-scattered light, and to make them interfere with each other, the phase of the scattered light is adjusted by the quarter-wave plate 5. In addition, the intensity of the non-scattered light is attenuated to almost comparable to the amplitude strength of the scattered light by attenuation filter 6. In this way, a phase contrast microscope image is provided by overlapping the scattered spherical wave and the non-scattered light on the imaging surface (on the detector 4).

In a conventional phase contrast microscopy method, one light source emitting light with a wavelength in transparency region to a specimen is used. This enable to illuminate a ground state specimen, and as shown in FIG. 1, the refractive index distribution is formed by such as molecule-intrinsic electron states and absorption bands corresponding to vibrational-rotational levels belonging to the each states.

Generally, in a conventional phase contrast microscopy method, the wavelength of this illuminating light is set to the photon energy as small as it will not excite the molecules to the S1 electron state. That is, in FIG. 3 (*a*), the wavelength is set to correspond to the photon energy ($E_p$) smaller than the energy gap ($E_1$) between S0 state and S1 state. In other words, as shown in FIG. 3 (*b*), a transparency region on the long-wavelength side of an absorption band is used and the phase contrast image is obtained by using a variation of refractive index generated in this region.

Figure 4:
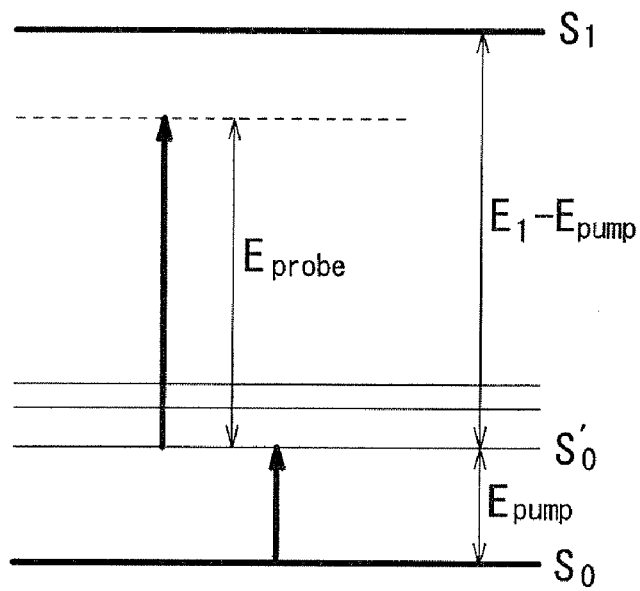
FIG. 4 is a figure to explain IR-visible double resonance process.
Figure 4:
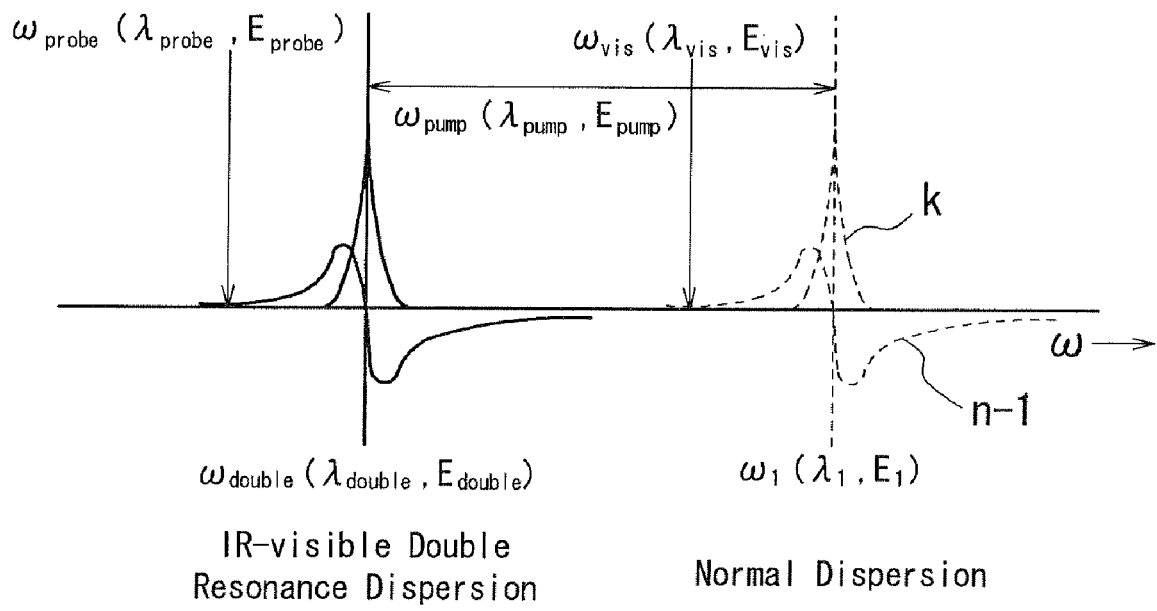

On the other hand, according to the present invention, a more interesting dispersion phenomenon can be induced by using IR-visible double resonance process and by coordinating irradiation condition of infrared light and visible light. This is shown in FIGS. 4 (*a*) and (b). FIG. 4 (*a*) shows that a molecule is excited to a vibrational-rotational level S0' belonging to the S0 state by infrared light of photon energy Epump, and that the molecule is irradiated by visible light of photon energy Eprobe simultaneously. Here, Eprobe is lower than the energy needed to make a molecule transit from the S0' state to the S1 state. In other words, the following condition is satisfied:

Eprobe<($E_1$–Epump)

Figure 3:
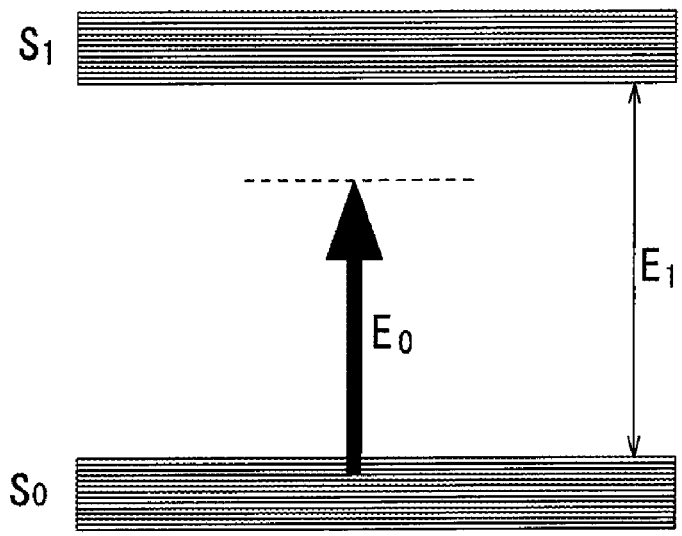
FIG. 3 shows photon energy of illumination light generally used in phase contrast microscopy and refractive index distribution of a specimen.
Figure 3:
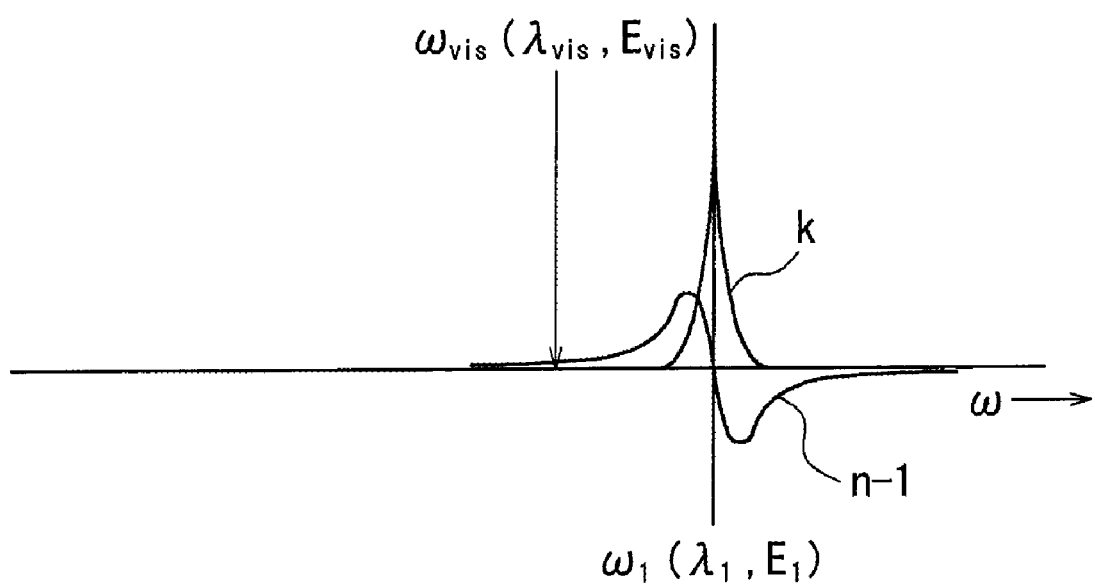

When infrared light is not irradiated to a molecule, as according to the conventional microscopy method, since the photon energy to transit from the S0 state to the S1 state is $E_1$ as indicated in FIG. 3, absorption occurs in the vicinity of this domain and dispersion phenomenon is observed. In other words, it is observed at the corresponding frequency domain $\omega_1$ and at wavelength $\lambda_1$ (Normal dispersion).

However, when infrared light is irradiated, as according to the present invention, an absorption band generated by double resonance of photon energy $E_1$-Epump (corresponding frequency domain: ωdouble, wavelength: λdouble) appears as shown in FIG. 4 (*b*). Thus, while irradiating infrared light, a dispersion phenomenon is observed in the neighboring domain of $E_1$-Epump (double resonance dispersion).

According to the present invention, an infrared ray is irradiated to a specimen as pump light, and probe light with photon energy $E_1$-Epump is also irradiated simultaneously, and phase contrast image of the probe light is observed. Here, the photon energy of the probe light is located at the lower energy side of the double resonance absorption band, namely long-wavelength side, and the photon energy of the probe light is away from the normal dispersion region and does not involve a double resonance absorption, so that the probe light is transparent to the specimen. However, since a phase lag in the probe light is generated by the double resonance dispersion, the probe light is scattered by the emergence of phase object, namely vibrationally excited molecule by pump light irradiation.

In other words, the phase contrast image obtained by the probe light is no other than visualized image of spatial distribution of the vibrationally excited molecules. This gives information equivalent to the conventional IR-visible double resonance microscopes. Moreover, the superior point of the present invention is quality of the obtained image with high S/N ratio, since it utilizes the phase contrast microscopy.

In particular, the present invention is superior in sensitivity because the variation of refractive index is traced. In an exemplified embodiment of the present invention, at first, phase contrast image of a probe light is measured on condition that no pump light is irradiated, and in the next step, the pump light is irradiated and phase contrast image of probe light is measured (phase contrast IR-visible double resonance microscope image). In this case, the image measured under the condition without irradiating pump light is regarded as background signal. Thus, by calculating the difference between the phase contrast IR-visible double resonance microscope image and the background image, it is possible to extract the strength component only of the spatial distribution of vibrationally excited molecules.

Even more particularly, molecules to be observed by the present invention does not necessarily be fluorescent molecules, and all that required is that the molecules have vibrational-rotational levels excitable by a light source and several higher electron states. Therefore, there occurs no decoloration problem like in conventional methods, and in particular, if the wavelength of the infrared light is adjusted to vibrational-rotational levels corresponding to various chemical groups, spatial distribution image of each chemical group can be obtained.

As thus described, according to the present invention, a specimen can basically be observed without staining. However, besides observation without staining, it is also effective to introduce markers. For example, in case of a living specimen, when selecting and observing such as a pathological region of interest, probe molecules which selectively combine with the region are introduced. In this state, all that is required for the probe molecules is to have photon energy (wavelength) suitable to the vibrational excitation levels or electron excited states corresponding to the pump light and probe light.

In addition, because a marker used in the present invention need not be a fluorescent marker like many of the markers now being used, it can be selected from wider range of molecules. For example, if an intercellular messenger substance is combined with a marker, in-vivo metabolic activity in a living body can be visualized as a phase contrast image with high sensitivity.

It is noted that, in case a fluorescent marker is selected, it is desirable that the wavelength of the probe light does not exist in the range of fluorescence wavelength of the marker molecule, because the fluorescence would be a background signal. From this viewpoint, the present invention is rather advantageous to apply to non-fluorescent molecules to obtain phase contrast image.

Examples of such non-fluorescent molecules are molecules having molecule side chain with high electron density including lone electron-pair (so-called n orbit). Fluorescence signal, which is identical to background signal, can be reduced in itself by selecting such molecules.

According to the present invention, limit of resolution, which is limited to several μm in case of measurement using only infrared light, can be improved to that of visible light (i.e. a few to several hundreds of nano meters) same as IR-visible double resonance microscope. As a matter of course, a three-dimensional cross-sectional image can also be obtained.

It is noted that the present invention is not limited to the combination of infrared light and visible light. The present invention basically excites a molecule to a specific quantum state by the first electromagnetic ray and detect a phase difference by means of dispersion induced by the quantum state intrinsic to the excited molecule. In other words, a spatial distribution image of molecules excited by the first electromagnetic ray is converted to a phase contrast image of the second electromagnetic ray. Therefore, it is also possible to excite molecules to a higher electron state by the first electromagnetic ray and measure the phase difference using dispersion by a still higher electron state by further irradiating another second electromagnetic ray.

Here, the electromagnetic ray usable to the present invention includes, in a broad sense, a microwave, terahertz wave, infrared light, visible light, ultraviolet light, extreme ultraviolet light, X-ray and gamma ray, and if electromagnetic ray of each wavelength band has absorption band due to quantum state transition, any two electromagnetic rays from these electromagnetic rays with two wavelengths can be combined and used. In addition, as for the specimen, as long as a quantum excited state can be generated by an electromagnetic ray with corresponding wavelength, the detection object is not limited to molecules, and it can be an atom, an atomic nucleus and a crystal as well as an artificial quantum structure like quantum dot.

Figure 5:
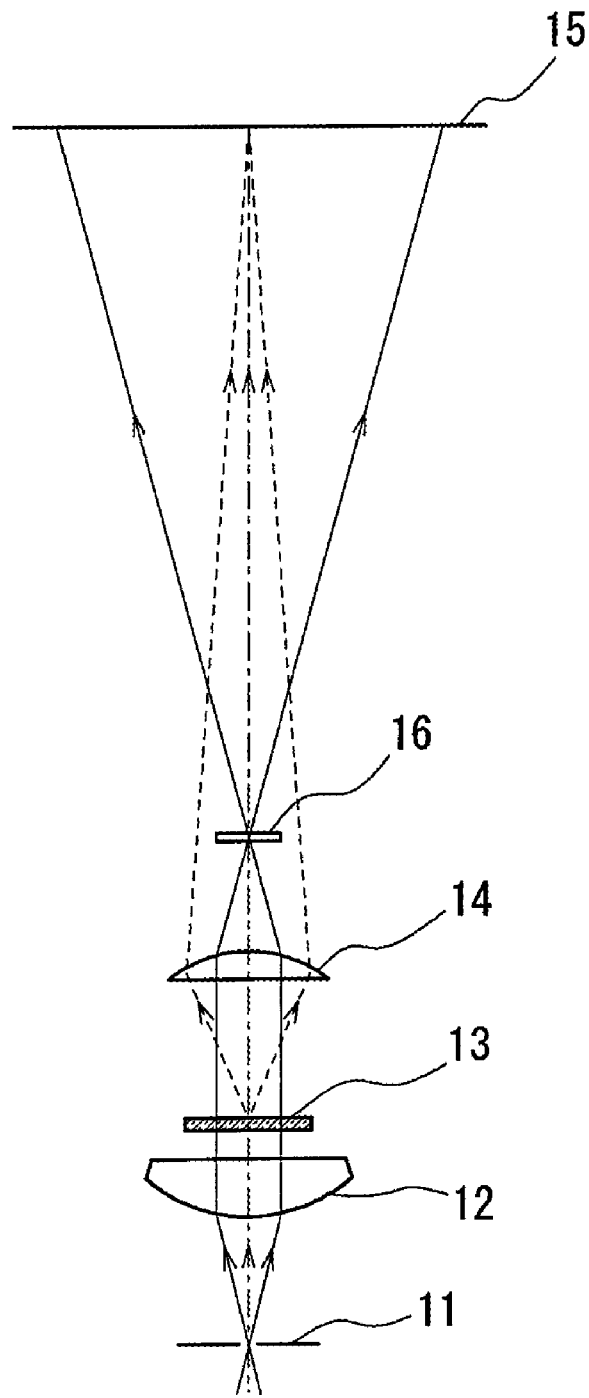
FIG. 5 is a figure to explain a typical phase contrast microscope which provides a basis of the present invention.

FIG. 5 illustrates a typical phase contrast microscope which provides a basis of the present invention. In this phase contrast microscope, illumination light from a light source which is not shown in the figure is converted to a spherical wave by passing through an aperture diaphragm 11, then converted to parallel light by an illumination lens 12 and is irradiated to a specimen 13, and then diffracted light which has phase difference to the illumination light (reference light) transmitting through the specimen 13 form an image on an imaging surface 15 by an object lens 14. A quarter wavelength plate 16 with a very small area is installed in an image side focus position of the object lens 14. This quarter wavelength plate 16 functions as a attenuating filter at the same time, and attenuates the reference light to amplitude intensity comparable to the diffracted light.

In this way, a phase contrast image is formed by making reference light and diffracted light interfere with each other on the imaging surface 15. Meanwhile, because the broadening of the diffracted light at an image side focus position of the object lens 14 is larger than the quarter wavelength plate 16, influence on the imaging surface is negligible.

Next, embodiments of the present invention are described below.

First Embodiment

Figure 6:
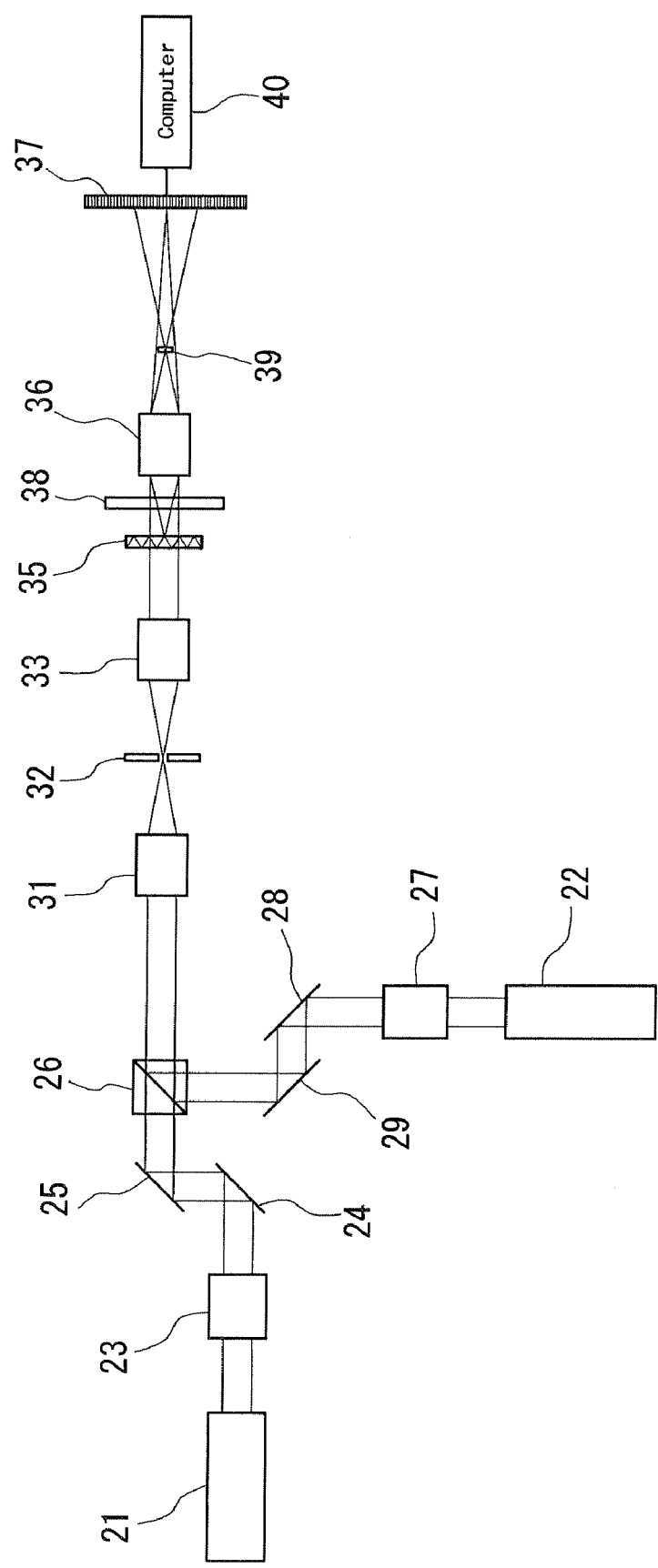
FIG. 6 is a schematic diagram of a microscope according to the first embodiment of the present invention.

FIG. 6 is a schematic diagram of a microscope according to the first embodiment of the present invention. This microscope is a phase contrast IR-visible double resonant microscope, which use a CW infrared optical parametric laser that is wavelength-tunable in infrared region, as a pump light source 21, namely the first radiation source, and a continuous-wave dye laser that is wavelength-tunable in visible region, as a probe light source 22, namely the second radiation source. The CW infrared optical parametric laser constituting the pump light source 21 can adjust its wavelength in 3 μm band by adjusting angle of the wavelength conversion crystal. In addition, the dye laser constituting the probe light source 22 can cover almost all of the visible regions by selecting dye which is the laser medium.

In this embodiment, an oscillation wavelength (pump light) of the pump light source 21 is synchronized with the wavelength which corresponds to the photon energy to make a molecule transit from the ground state S0 to the vibrational excitation level S0'. In addition, an oscillation wavelength (probe light) of the probe light source 22 is synchronized with the wavelength which corresponds to the photon energy lower than the energy needed to make a molecule transit from the S0' state to the S1 state. For example, in case the observation object is rhodamine 6G, the wavelength of the pump light is set to 3.1 μm, and the wavelength of the probe light is set to 640 nm. In this case, for example, rhodamine B is suitable for dye in the dye laser 22.

The pump light, i.e. the first electromagnetic ray, emitted from the pump light source 21 is modulated to a pulsed light by Electro-Optical Modulator (EOM) 23, if necessary, and after being aligned with an optical axis of a dichroic prism 26 by deflecting mirror 24 and 25, then it enter the dichroic prism 26. In the same way, the probe light, i.e. the second electromagnetic ray, emitted from the probe light source 22 is modulated to a pulsed light by Electro-Optical Modulator (EOM) 27, if necessary, and after being aligned with the optical axis of the dichroic prism 26 by deflecting mirror 28 and 29, then enter the dichroic prism 26. In this way, the pump light and the probe light are aligned concentrically in the dichroic prism 26 and exit from there. In addition, EOM 23 acts as a shutter of the pump light, and EOM 27 acts as a shutter of the probe light, as well.

A pinhole illuminating lens 31 allows the light exited from the dichroic prism 26 to pass through a pinhole 32 and the light is converted to a spherical wave. Then, the spherical wave is further converted to a plane wave by a specimen illuminating lens 33, and then irradiate a specimen 35. Thus, in this embodiment, the illumination optical system is so configured as to have the dichroic prism 26, the pinhole-illuminating lens 31, the pinhole 32 and the specimen-illuminating lens 33.

Diffracted light generated by spatial variation of refractive index caused by irradiation of the pump light and the probe light forms an image on a CCD camera 37 as an image pickup device by an object lens 36, along with the non-diffracted probe light.

In addition, a band-pass filter 38 is placed between the specimen 35 and the object lens 36 in order to cut off the pump light, so that only the probe light can reach a the CCD camera 37. In addition, a quarter wavelength plate 39 is placed at the image side focus position of the object lens 36, in order to make a phase shift of the non-diffracted probe light (reference light) and to make the amplitude strength of the probe light attenuate comparable to the diffracted light. In this way, the reference light and the diffracted light are overlapped on the CCD camera 37, and a phase contrast image of the specimen 35 is formed. The image signal provided from this CCD camera 37 is input to a computer 40 and is processed therein. Thus, in this embodiment, the detection means is so configured as to have the object lens 36, the CCD camera 37, the band-pass filter 38, the quarter wavelength plate 39 and the computer 40.

In this embodiment, at first, the pump light is blocked off by the EOM 23 and only the probe light is irradiated to the specimen 35, and then a phase contrast image formed on the CCD camera 37 by the sole irradiation of the probe light is imported to the computer 40. Next, the EOM 23 is opened and both of the pump light and the probe light are irradiated to the specimen 35 simultaneously, then the phase contrast image formed on the CCD camera 37 is imported to the computer 40. It is noted that the order of the acquisition of the phase contrast image by the single probe light and the acquisition of the phase contrast image by the pump light and the probe light can be inverted.

Here, because the phase contrast image formed by the sole irradiation of the probe light is identical to the background light, an arithmetic processing in which phase contrast image components by the sole irradiation of the probe light is deducted from the phase contrast image formed by the simultaneous irradiation of the pump light and the probe light is performed in the computer 40, and thus the phase contrast IR-visible double resonance microscope image is obtained. Accordingly, if a molecule of the observation object is rhodamine 6G, a spatial distribution image of CH groups can be obtained. The phase contrast IR-visible double resonance microscope image thus obtained is appropriately processed such as being displayed on a display device not shown in the figures and being stored in a storage device.

In addition, it is also possible to observe a time response of the image with respect to each pulse, for example, by controlling the EOMs 23 and 27 to be pulse-driven synchronously in the order of nano seconds to generate pulsed lights of both of the pump light and the probe light. Furthermore, in this case, irradiation period of the pulsed probe light and the pulsed pump light can be relatively adjusted. Thus, in this case, the pulsed light sources are so configured as to have the EOM 23 and the EOM 27.

Next, a case in which the specimen 35 includes porphyrin is explained. Porphyrin is a molecule included in a living body, and has scattered vibrational absorption bands of NH group near the 2.8 μm wavelength, as well as a strong absorption band in the visible region of near 500 nm due to electron transition. Therefore, in this case if, the wavelength of the probe light is set to, for example, 600 nm, the probe light is not absorbed and fluoresce is not emitted.

The microscope in this case can be configured, for example in FIG. 6, by adjusting the oscillation wavelength of the pump light source 21 to 2.8 μm, as well as by adjusting the oscillation wavelength of the probe light source 22 to 600 nm, and by replacing the bandpass filter 38 to the one which can cut off pump light of 600 nm wavelength. Hereby, the specimen 35 including porphyrin can be observed without staining.

The molecules to be observed are not limited to those which include CH groups or NH groups as stated above but the molecules which include any one of the chemical groups in C≡C, C=C, C=C=C, C=C=C=C, CH, CO, C—C, C=N, C—C—CN, C—C=C, N=C=O, N=C=N, C=N, NNN, N=N, C—N, ONO, N=O, O—O, SH, CS, S—S, $SO_2$, S=O, C—S—C, OH, NH, $CO_3$, $CH_3$—C, CH—(C=O), —$CH_2$—, —$CH_2$— (C=O), —$CH_2$— (C=N), >C=$CH_2$, >C=CH—, —C=C—H, —C—C—, —CO—OH, P=O, Si—$CH_3$, CF, $CCl_2$, $CCl_3$, P=S, Si—C, $CH_2$—S—$CH_2$, $C_6H_6$—P, R—O—$SO_2$—O—R, R—O—$SO_2$—R, H—CO—O—R, —$CH_3$—CO—C—R, =CH—CO—O—R, $C_6H_6$—CO—O—R, $CH_2$—CHO, $C_6H_6$—CHO, $CH_2$—CO—$CH_2$, $C_6H_6$—CO—C, C—CO—CO—C, —CO—$NH_2$, —CO—NH—R, —CO—$NR_2$, $CH_2$—$NH_2$, >CH—$NH_2$, $C_6H_6$—$NH_2$, $CH_2$—NH—$CH_2$, CH—NH—CH, $(CH_2)_3$N, $C_6H_6$—N—$R_2$, >C=NH, >C=N—C, —C=N, PH, SiH, O=C(O—R)$_2$, HN=C(O—R)$_2$, R—O—$NO_3$, R—$NO_2$, R—O—NO, $CH_2$—O—$CH_2$, $C_6H_6$—O—$CH_3$, $CH_2$—OH, CH—OH, C—CH, $C_6H_6$—OH, R—SO—R, R—$SO_2$—R, R—$SO_2$—$NH_2$ can also be excited by pump light corresponding to the intrinsic vibrational excitation levels and can be measured in the same way, so that the spatial distribution of the vibrational excitation levels belonging to each molecule can be mapped by the phase-contrast method as well.

Second Embodiment

In the second embodiment, ultraviolet ray and X-ray are used, in place of the infrared light and the visible light in the first embodiment.

Figure 7:
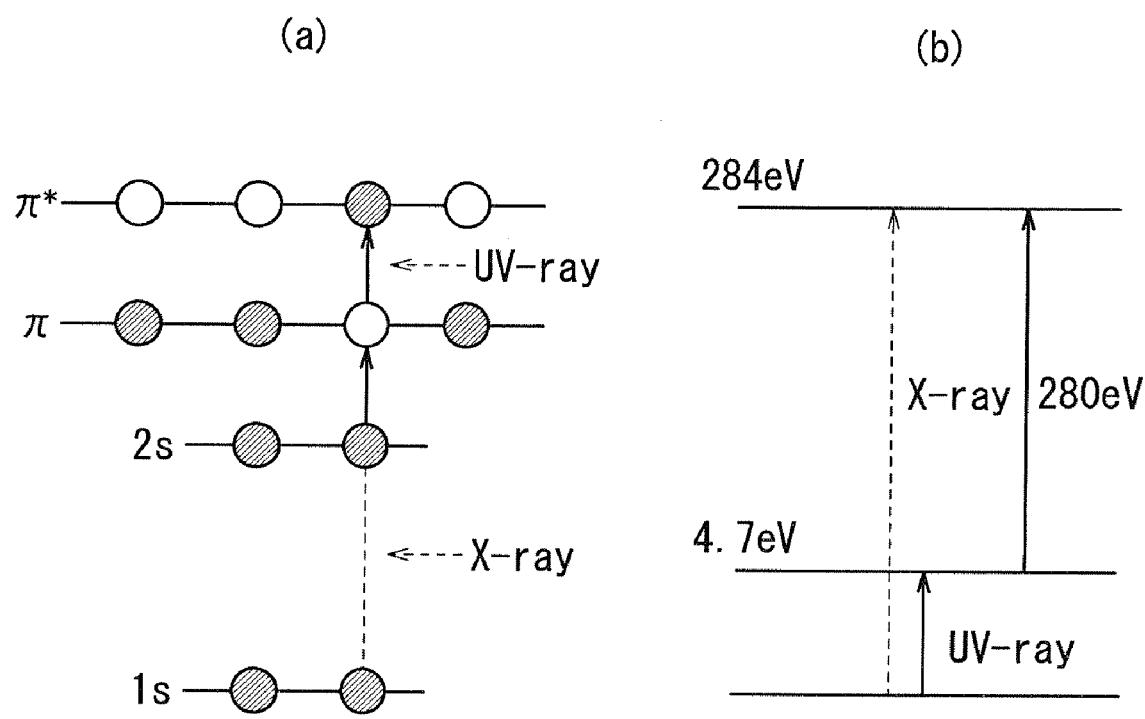
FIG. 7 is a figure to explain the double resonance absorption process in which an electron state of benzene and carbon 1s electron in an inner shell are involved.

FIGS. 7 (a) and (b) show the double resonance absorption process in which an electron state of benzene and carbon 1s electron in an inner shell are involved. In this case, a valence electron of benzene is excited to a π* orbit by the ultraviolet ray, then, by X-ray, a carbon 1s electron is resonantly absorbed in the valence electron orbit which has become a hole. Here, the energy that is necessary for excitation of a valence electron is about 4.7 eV, so that the valence electron can be excited by an ultraviolet (UV) ray of around 260 nm.

On the other hand, the energy needed for a carbon 1s electron to be resonantly absorbed in the outer π* orbit is about 284 eV. Thus, in this case, the UV ray serves as a pump light, and, the X-ray serves as a probe light. Here, the energy of the probe light needs to be lower than the value that is obtained by subtracting 4.7 eV, which is photon energy of the UV excitation light, from about 284 eV. In other words, it needs to be lower than 279 eV, which corresponds to 4.4 nm wavelength.

Figure 8:
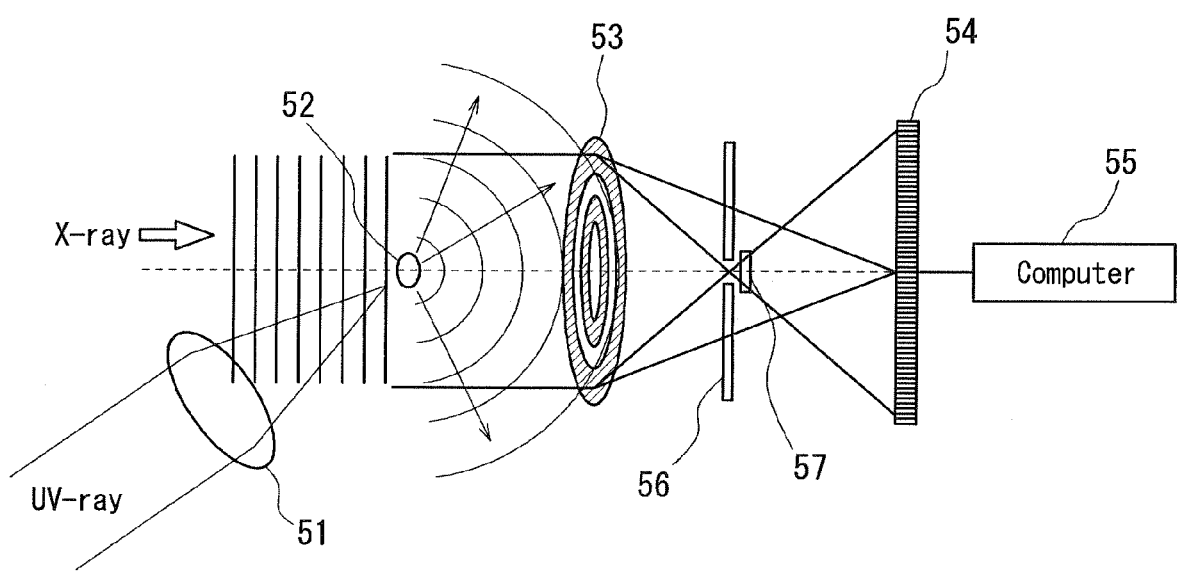
FIG. 8 is a schematic diagram of the microscope according to the second embodiment of the invention.
Figure 9:
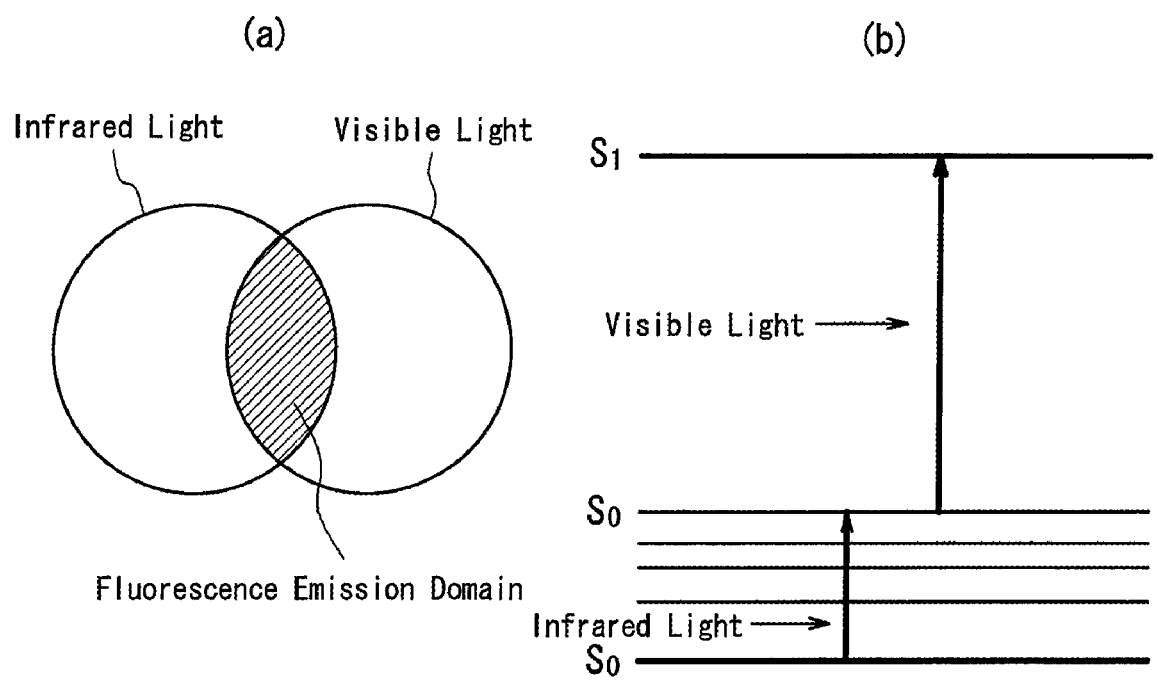
FIG. 9 is a figure to explain IR-visible double resonance microscopy.
Figure 10:
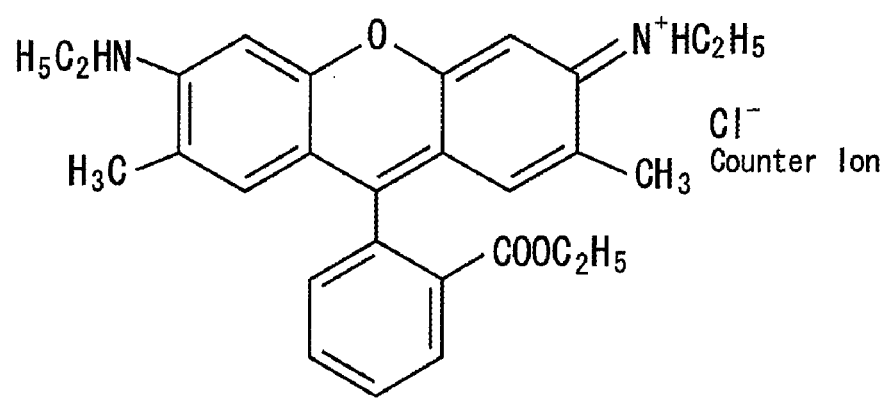
FIG. 10 shows a molecular structure of rhodamine 6G and its energy diagram.
Figure 10:
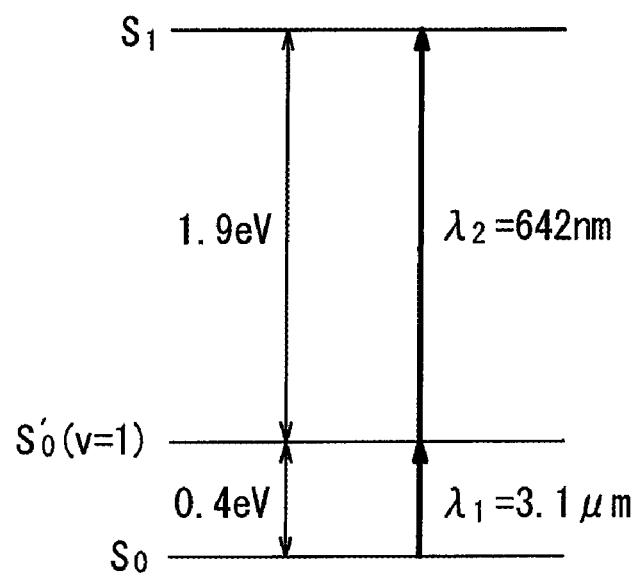

FIG. 8 is a schematic diagram of the microscope according to the second embodiment. In this embodiment, an Nd:YAG laser, for example, is used as a pump light source, and UV ray which is fourth-harmonic wave (266 nm) of the fundamental wave is irradiated to the specimen 52 by way of an illumination lens 51. In addition, as for the probe light source, a synchrotron is used for a variable wavelength and X-ray tube with a carbon target (4.4 nm emission wavelength, i.e. Carbon K-α line) is used for a fixed wavelength, and the X-ray is irradiated to the specimen 52 as plane wave.

Along with non-diffracted X-ray, the diffracted light generated by the spatial variation of refractive index in the specimen 52 caused by irradiation of UV ray and X ray provides an image on CCD camera 54 by means of Fresnel zone plate 53, which is known as an imaging optical element for X-ray frequency region, and form a phase contrast image of the specimen 52 by interference and then the phase contrast image is imported to a computer 55.

In addition, a quarter wavelength plate 56 with a pinhole is placed at an image side focus position of Fresnel zone plate 53 for phase adjustment of the diffracted light, and, at the same time, an attenuating filter 57 for attenuating the non-scattered light is placed at the pinhole. Here, the quarter wavelength plate 56 can be composed of, for example, a graphite film or a polyethylene membrane, and the attenuating filter 57 can be composed of a boron film filter which has a function to cut off UV ray and to let X-ray pass through.

In this embodiment, same as the first embodiment, the specimen 52 is preferably irradiated at first by an X-ray alone, and the phase contrast image formed on the X-ray CCD camera 54 by the sole irradiation of the X-ray is imported to the computer 55. Next, a UV ray and an X-ray are irradiated to the specimen 52 simultaneously, and a phase contrast image formed on the X-ray CCD camera 54 is captured and imported to the computer 55. After that, in the computer 55, an arithmetic processing to deduct the component of the phase contrast image by the separate irradiation of the X-ray from the phase contrast image formed by the simultaneous irradiation of the UV ray and the X-ray is performed, and thus a phase contrast UV- and -X-ray double resonance microscope image is obtained. It is noted that, while Fresnel zone plate 53 is used as an imaging optical element for X-ray frequency region in FIG. 8, a reflecting objective Schwarzshild type optical system with mirror-surfaced multilayered membrane may also be used.

Molecules to be observed according to this embodiment include, for example, tyrosine, phenylalanine and tryptophan, which have a benzene ring and are basic biological molecules constituting protein. In this case, spatial distribution of the benzene rings which π* orbits included in these molecules have excited can be obtained.

The present invention is not limited to the embodiments described above, and many variants and modifications are possible within the scope of the invention. For example, in the second embodiment, phase contrast image showing spatial distribution of nucleic-acid bases such as adenine, thymine, cytosine, guanine and uracil can also be obtained, since a nitrogen base, for example, also has an almost the same electronic structure as a benzene ring. Thus, the observation object of the present invention is not limited to molecules, but the invention may also be effectively applied if a material to be observed has quantum mechanical resonant levels such as vibration, rotation, electron excitation and nuclear excitation, and double resonance by the combination of each level is possible.

In addition, since spatial distribution of excited state existing in a specimen in itself is visualized as phase contrast information in the present invention, it is also possible to stain the selected observation area with a maker which has a characteristics to selectively bind chemically to the area in order to positively highlight the selected area. The marker in this case may be, for example, an atom, an atomic nucleus, a crystal, or even an artificial quantum structure like quantum dot. For example, a semiconductor quantum dot may be introduced into CdSe. In particular, because CdSe can be made bound with various chemical modified bases by coating surface with ZnS, the observation area can be highlighted.

What is claimed is:

1. A microscopy method for a microscope, comprising:
   simultaneously irradiating a specimen with first and second electromagnetic rays having different wavelengths, wherein the rays at least partly overlap each other; and
   visualizing a spatial distribution of a refractive index variation as a phase contrast image of the second electromagnetic ray having passed the specimen in a region of the specimen to which the overlapped first and second electromagnetic rays are simultaneously irradiated;
   wherein the first electromagnetic ray has a wavelength or a photon energy which excites a predetermined substance in the specimen from a ground state to a quantum state that is different from the ground state.

2. The microscopy method according to claim 1, wherein the first electromagnetic ray has a wavelength or a photon energy that excites the predetermined substance in the specimen from the ground state to a vibrational-rotational level belonging to the ground state.

3. The microscopy method according to claim 2, wherein the second electromagnetic ray has a photon energy at least less than a difference between an amount of energy required to excite the predetermined material in the specimen from the ground state to a first electron-excited state and an amount of energy required to excite the material from the ground state to the vibrational-rotational level belonging to the ground state.

4. The microscopy method according to claim 1, wherein the region irradiated by the second electromagnetic ray in the specimen is smaller than the region irradiated by the first electromagnetic ray.

5. The microscopy method according to claim 4, wherein the specimen is stained by molecules which have a vibrational-rotational level that is vibrationally-excitable with the first electromagnetic ray.

6. The microscopy method according to claim 4, wherein the specimen is stained by molecules, and wherein an energy difference of the molecules between a first electron-excited state and a vibrational-rotational level belonging to the ground state is greater than a photon energy of the second electromagnetic ray.

7. The microscopy method according to claim 4, wherein the specimen has a vibrational-rotational level that is vibrationally-excitable with the first electromagnetic ray, wherein the specimen is stained by molecules, and wherein an energy difference of the molecules between a first electron-excited state and the vibrational-rotational level belonging to the ground state is greater than a photon energy of the second electronic magnetic ray.

8. The microscopy method according to claim 2, wherein the predetermined substance in the specimen comprises non-fluorescent molecules.

9. The microscopy method according to claim 3, wherein the specimen comprises molecules including any of: C=C, C≡C, C=C=C, C=C=C=C, CH, CO, C—C, C≡N, C—C—CN, C—C≡C, N=C=O, N=C=N, C=N, NNN, N=N, C—N, ONO, N=O, O—O, SH, CS, S—S, $SO_2$, S=O, C—S—C, OH, NH, $CO_3$, $CH_3$—C, CH—(C=O), —$CH_2$—, —$CH_2$—(C=O), —$CH_2$—(C=N), >C=$CH_2$, >C=CH—, —C≡C—H, —C≡C—, —CO—OH, P=O, Si—$CH_3$, CF, $CCl_2$, $CCl_3$, P=S, Si—C, $CH_2$—S—$CH_2$, $C_6H_6$—O—P, R—O—$SO_2$—O—R, R—O—$SO_2$—R, H—CO—O—R, —$CH_3$—CO—C—R, =CH—CO—O—R, $C_6H_6$—CO—O—R, $CH_2$—CHO, $C_6H_6$—CHO, $CH_2$—CO—$CH_2$, $C_6H_6$—CO—C, C—CO—CO—C, —CO—$NH_2$, —CO—NH—R, —CO—$NR_2$, $CH_2$—$NH_2$, >CH—$NH_2$, $C_6H_6$—$NH_2$, $CH_2$—NH—$CH_2$, CH—NH—CH, $(CH_2)_3$N, $C_6H_6$—N—$R_2$, >C=NH, >C=N—C, —C≡N, PH, SiH, O=C(O—R)$_2$, HN=C(O—R)$_2$, R—O—$NO_3$, R—$NO_2$, R—O—NO, $CH_2$—O—$CH_2$, $C_6H_6$—O—$CH_3$, $CH_2$—OH, CH—OH, C—CH, $C_6H_6$—OH, R—SO—R, R—$SO_2$—R, R—$SO_2$—$NH_2$.

10. The microscopy method according to claim 8, wherein the molecules include lone electron excitation.

11. The microscopy method according to claim 1, wherein the wavelength of the first electromagnetic ray exists within a range of a resonant absorption band corresponding to an excitation transition of the predetermined substance in the specimen from the ground state to a first electron-excited state.

12. The microscopy method according to claim 1, wherein the second electromagnetic ray has a photon energy less than an excitation energy required for a transition of the predetermined substance in the specimen from a first electron-excited state to another excited state of a higher energy level than an energy level of the first electron-excited state.

13. The microscopy method according to claim 12, wherein a range of the wavelength of the second electromagnetic ray is outside of a fluorescence wavelength range.

14. The microscopy method according to claim 13, wherein the wavelength of the first electromagnetic ray exists within a range of a resonant absorption band corresponding to an excitation transition of the predetermined substance in the specimen from the ground state to the first electron-excited state, wherein the specimen is stained by molecules, and wherein the excitation energy required for the transition of the molecules from the first electron-excited state to another electron-excited state of a higher energy level than the energy level of the first electron-excited state is greater than the photon energy of the second electromagnetic ray.

15. The microscopy method according to claim 1, further comprising:
   separately irradiating the specimen solely with the second electromagnetic ray;
   separately visualizing a spatial distribution of a refractive index variation generated in a region of the specimen irradiated solely by the second electromagnetic ray as a phase contrast image; and
   generating a difference image between (i) the phase contrast image of the second electromagnetic ray having passed through the specimen in the region of the specimen to which the overlapped first and second electromagnetic rays are simultaneously irradiated, and (ii) the phase contrast image of the separately visualized spatial distribution of the refractive index variation generated in the region of the specimen irradiated solely by the second electromagnetic ray.

16. A microscope comprising:
   a first radiation source which generates a first electromagnetic ray;
   a second radiation source which generates a second electromagnetic ray, wherein the second electromagnetic ray has a wavelength that is different from a wavelength of the first electromagnetic ray;
   an illumination optical system configured so that the first electromagnetic ray generated from the first radiation source and the second electromagnetic ray generated from the second radiation source are irradiated to the specimen with the rays at least partly overlapping each other; and
   detection means for visualizing a spatial distribution of a refractive index variation as a phase contrast image of the second electromagnetic ray passing through the specimen in a region of the specimen to which the overlapped first and second electromagnetic rays are irradiated;
   wherein the first electromagnetic ray has a wavelength or a photon energy which excites a predetermined substance in the specimen from a ground state to a quantum state that is different from the ground state.

17. The microscope according to claim 16, wherein at least one of the first radiation source and the second radiation source comprises a wavelength-tunable laser light source.

18. The microscope according to claim 16, wherein at least one of the first radiation source and the second radiation source comprises pulsed light sources.

19. The microscope according to claim 16, wherein the first radiation source and the second radiation source comprise pulsed light sources which can relatively adjust radiation periods of the first electromagnetic ray and the second electronic magnetic ray respectively.

20. The microscope according claim 16, wherein the detection means includes means for eliminating the first electromagnetic ray having passed through the specimen.

21. The microscopy method according to claim 9, wherein the molecules include lone electron excitation.

22. The microscope according to claim 17, wherein at least one of the first radiation source and the second radiation source comprises pulsed light sources.

23. The microscope according to claim 17, wherein the first radiation source and the second radiation source comprise pulsed light sources which can relatively adjust radiation periods of the first electromagnetic ray and the second electronic magnetic ray respectively.

* * * * *